United States Patent [19]

Lembke et al.

[11] 4,255,414

[45] Mar. 10, 1981

[54] EDIBLE OR ORAL COMPOSITIONS

[75] Inventors: Andreas Lembke, Eutin-Sielbeck; Dietrich Gorny, Frankfurt am Main, both of Fed. Rep. of Germany

[73] Assignee: Ferrero GmbH, Frankfurt am Main, Fed. Rep. of Germany

[21] Appl. No.: 6,305

[22] Filed: Jan. 24, 1979

[30] Foreign Application Priority Data

Jan. 31, 1978 [DE] Fed. Rep. of Germany ....... 2804093

[51] Int. Cl.³ .................. A61K 7/28; A61K 37/48
[52] U.S. Cl. ........................ 424/50; 424/94
[58] Field of Search .......... 424/48, 49, 50, 94, 424/180, 343; 426/361, 548, 658, 660

[56] References Cited

U.S. PATENT DOCUMENTS

| | | | |
|---|---|---|---|
| 3,075,884 | 1/1963 | Bilotti et al. | 424/48 |
| 3,194,738 | 7/1965 | Harrison et al. | 424/48 |
| 3,574,824 | 4/1971 | Echeandia et al. | 424/50 |
| 3,751,561 | 8/1973 | Wildi et al. | 424/48 |
| 3,914,434 | 10/1975 | Bohni | 424/343 |
| 4,082,841 | 4/1978 | Pader | 424/50 |
| 4,107,291 | 8/1978 | Ishibashi | 424/48 |
| 4,133,875 | 1/1979 | Hillman | 424/50 X |
| 4,150,113 | 4/1979 | Hoogendoorn et al. | 424/50 |
| 4,153,732 | 5/1979 | Muhler | 426/72 |
| 4,157,386 | 6/1979 | La Rochelle | 424/52 |

FOREIGN PATENT DOCUMENTS

| | | | |
|---|---|---|---|
| 751739 | 11/1970 | Belgium | 424/50 |
| 753877 | 12/1970 | Belgium | 424/50 |
| 756289 | 3/1971 | Belgium | 424/50 |
| 1927411 | 12/1970 | Fed. Rep. of Germany | 424/50 |
| 1033229 | 6/1966 | United Kingdom | 424/50 |
| 1270200 | 4/1972 | United Kingdom | 424/50 |

*Primary Examiner*—Shep K. Rose
*Attorney, Agent, or Firm*—Sughrue, Rothwell, Mion, Zinn and Macpeak

[57] ABSTRACT

Edible or oral compositions which limit the promotion of tooth decay and comprise lactate dehydrogenase and sucrose-inverting enzymes. Included among such compositions are foods containing 0.1 to 2% water and either sugar or sugar substitutes. Foods without sugars and pharmaceutical preparations are also included in the scope of this invention.

45 Claims, No Drawings

EDIBLE OR ORAL COMPOSITIONS

DESCRIPTION OF THE INVENTION

This invention relates to edible or oral compositions. More particularly the invention is directed to food containing sugar and very little water and to pharmaceutical preparations, in particular hygiene agents for tooth and mouth care, containing little water.

It is known that in the oral cavity micro-organisms, foodstuffs, beverages and medicaments with a high sugar content lead, in the presence of micro-organisms, to the formation of so-called "plaques", and acid decomposition products which severely attach tooth enamel. This effect is known by the names caries. Caries is understood to be an initial attach on the surface of teeth which are then progressively destroyed by cavities being formed therein.

Those micro-organisms which are present in or under the films on teeth, called plaques, are of prime importance for the development of dental caries. As with all other germs present in the oral cavity, the micro-organisms present in the dental plaques live on the food residues remaining in the mouth after the intake of food. Low-molecular carbohydrates, above all various types of sugars, are particularly acceptable to the bacteria because they are the best sources of energy for the intensive growth and metabolism processes of the bacteria.

The mechanism of the formation of caries does not yet appear to be fully understood. Cariogenic microbes, for example Streptococcus mutans, form the ferment dextran saccharase which breaks sucrose down into anhydroglucose and fructose. The anhydroglucose molecules can then accumulate, forming polymeric molecules which are called dextran gels. Amongs these, especially those dextran gels with a molecular weight of 10,000 to 200,000 have a particular adhesion. These dextran gels serve to a certain extent as "adhesives", which hold the bacteria concerned firmly on the surfaces of the teeth, that is to say which form plaques. Under the plaques and with exclusion of air, the bacteria mentioned can then produce, for example from sugar which has diffused in, acids, such as, for example, lactic acid or other acids which destory teeth, and this leads to the formation of first lesions of the enamel (initial caries), that is to say corrosion of the dentine, with the known, consequential results.

After the plaques have formed, calcium and phosphate are gradually dissolved out, especially form the apatite of tooth enamel, under the action of acid during the carious demineralisation taking place under the plaques.

Two directions have been adopted in attempts made hitherto to inhibit caries. These consist, in principle, of either increasing the resistance of the hard substance of teeth to attach by acid or of weakening the attack on the teeth by acid.

The first-mentioned solution to the problem includes experimental fluoridation of drinking water, salt or milk, which has been carried out on a large scale in the U.S.A. and in Switzerland. Furthermore, local application of fluoride-containing tablets and the use of fluorinated compounds, such as sodium fluoride, sodium monofluorophosphate, tin fluoride/calcium pyrophosphate or amine fluoride, may also be mentioned. Although, according to reports, a decrease in carious lesions by this means has been reported (sic), the results achieved are still unsatisfactory. Moreover, there are considerable reservations, also of a physiological nature, against introducing chemicals into, in particular, drinking water and foodstuffs such as milk. In addition, with the present diet of the civilian population, collective and individual fluoridation measures are not sufficient to counteract carious decay of teeth.

Attempts have also been made, however, to combat caries by controlling the formation of dextran, for example by the action of chemicals. The use of sodium oleate and linoleate for this purpose has been described in "Journal of Dental Health", volume 22, No. 4, December 1972, for example. The action of the sodium oleate and linoleate, according to German Offenlegungsschrift No. 2,442,825 on the formation of dextran, is said to be further increased by water-soluble secondary phosphates in agents for dental hygiene. The use of Ca salts, Na salts or Mg salts or esters of phosphoric acid with sucrose, glucose or lactose for the manufacture of dental hygiene products having a cariostatic action in the oral cavity has also been considered in German Auslegeschrift No. 1,467,809. These measures of blocking the metabolism of microflora in the mouth, which use the dextran/sucrose/enzyme system for producing the dental plaques, have indeed brought about a certain improvement of dental hygiene agents, but have not brought about the desired decisive combating of carious tooth decay.

The known attempts to utilise the lyolysis principle, that is to say, to prevent caries either by destroying the cariogenic micro-organisms by complete or partial disintegration, or by complete or partial disintegration of the adhesive dextran gels, have also hitherto been unsatisfactory. Accordingly, the destruction of or attach on cariogenic microbes by enzymes which have been isolated from certain strains of Streptococcus is disclosed in German Auslegeschrift No. 2,011,935. Three defined strains and their incorporation into dental hygiene agents have been given for this purpose. Moreover, the lyolysis principle has also been applied to dextran which has already been formed, using the enzyme dextranase according to German Offenlegungsschrift No. 1,955,956. Nevertheless, according to EURATOM (sic) Patent No. 318,815, the dextranase was capable of decomposing only soluble dextran, since insoluble dextran contains a proportion of mutan (sic) which cannot be attacked by dextranase. The use of "mutanase" has therefore been proposed in this Austrian Publication.

However, these attempts to improve dental hygiene agents by the disintegration of the micro-organisms producing dextran, or the dextrans themselves, and to incorporate systems of this type in dental hygiene agents have also not hitherto been completely satisfactory. This is partly attributable to the fact that it is not always possible to clean the teeth after each meal or after sweets and the like have been eaten, and that the usual action of dental hygiene agents on their own does not sufficie to stop damage occurring in the meantime.

Replacing some or all of the sucrose by other, non-cariogenic sugars or sugar alcohols or by artificial sweeteners was envisaged as a further way of combating caries.

In many applications it is not possible for technological, economic, organoleptic or medical reasons to complete replacement of sucrose by sugar substitutes which have a low cariogenic action or are non-cariogenic, for example by the sugar alcohols xylitol and sorbitol.

Amongst the artificial sweeteners, saccharin, one of the best known and most frequently used sugar substitutes, has the disadvantage that it produces an aftertaste which is unpleasant to the consumer. The medical profession is making known the serious reservations they have with regard to the harmful nature of other substances, for example the cyclamates. Artificial sweeteners have the disadvantage that, because of the high sweetening power, the small amounts to be used are not easy to meter, for example an "empty taste" is spoken of in this connection, that is to say the desired "body" is missing. Physiological effects also hamper general use of these artificial sweeteners.

The use of enzymes has also been recommended. Also the addition of invertase during the manufacture of individual specific foodstuffs is already known. Thus, invertase has found acceptance in the manufacture of artificial honey and in the liqueur, ice-cream and confectionery industries, where they are used for producing soft, stable cream fillings or for keeping marzipan soft. However, the foodstuffs forming the end products manufactured by this procedure contain no invertase, or at least no significant proportion of invertase. In addition, the use of α-glucosidases and/or β-fructosidases for precenting plaque formation is proposed in German Offenlegungsschrict No. 1,927,411. Furthermore, a polymer-enzyme compound which contains neutral, alkaline and acid proteases, in addition to amylase, lipase and dextranase, for decomposing food residues remaining in the mouth, has been described in German Offenlegungsschrift No. 1,948,298.

In spite of these numerous attempts to combat caries, which are based on the most diverse principles, there still exists an urgent need for additional or improved measures for preventing the harmful results of attack by acid in the presence of cariogenic micro-organisms in order to make the suppression of caries possible in the case of a conventional diet.

An object of the present invention is to counteract the harmful effects of caries both by improving conventional foodstuffs of low water content, which have been prepared using sugars, and optionally in addition by simultaneously improving dental hygiene agents and pharmaceutical preparations. The improvement of foodstuffs should particularly take into account the fact that the cariogenic attack takes place in the intervals of time between the customary periods of cleaning the teeth. In particular, it is intended, according to the invention, to convert foodstuffs into foodstuffs "which are not harmful to teeth" by adding a physiologically acceptable substance, with or without complete replacement of the sugars customarily used for this.

According to the present invention there is provided an edible or oral composition which composition contains sugar and, sugar substitutes or no sugar very litter water and having a content of the enzymes lactate dehydrogenase and saccharose—inverting enzyme which limits promotion of tooth decay. Sugar alcohols can be used as sugar substitutes.

Surprisingly, it has been found in the experiments according to the invention that carious attack was drastically reduced by the addition of lactate dehydrogenase together with a sucrose-inverting enzyme. When a diet was provided which contained, in addition to a high proportion of sucrose, a combination of the two enzymes envisaged according to the invention, the number of caries lesions was exceptionally low.

It is assumed that by adding lactate dehydrogenase in combination with a sucrose-inverting enzyme, an inhibition system is incorporated into foodstuffs and confectionery of low water content or containing no water, and when these products are eaten, this system counteracts the harmful effect, in the presence of cariogenic bacteria, of the products formed by the decomposition of sugars, and converts the foodstuffs, in particular confectionery, and the pharmaceutical preparations into non-cariogenic or anti-cariogenic foodstuffs and pharmaceutical preparations which are not harmful to teeth.

Foodstuffs "of low water content" are those foodstuffs having a moisture content so low that the enzymatic reaction is not initiated. By this there are preferably understood foodstuffs with a residual moisture of 0.1 to 2%.

By "sugar-containing" foodstuffs is meant those foodstuffs which contain a proportion of naturally occurring sugars, such as sucrose, glucose, fructose and the like. Foodstuffs containing sucrose are particularly preferred. It is known in the case of certain foodstuffs of low water content, sucrose has considerable technological advantages compared with other types of sugars.

If appropriate, even such foodstuffs or confectionery or pharmaceutical preparations which contain no customary sugars or which are essentially sugar-free can be used. These can be materials which are sweetened on the basis of sugar substitutes, for example with saccharin, cyclamate, protein sweeteners extracted from tropical plants, xylitol and the like. However, they can also be products which naturally contain essentially no sugar constituent and also do not require significant sweetening. In the case of this type of confectionary it is also advantageous to incorporate lactate dehydrogenase together with a sucrose-inverting enzyme. When the foodstuff is eaten, a proportion of these additives can in fact remain in the oral cavity together with the food residues adhering to the teeth and can there render harmless, for example, cariogenic products resulting from the decomposition of carbohydrates.

The expression "sugar-containing foodstuffs of low water content", however, is intended to comprise, in particular, confectionery. Examples of confectionery or closely related products are bakery products, desserts and artificial honey. Products of particular interest are so-called stimulants, such as various types of sweets, that is to say hard and soft toffees (bonbons), fondant, meringue wares, gum-type confectionery, liquorice, dragees, fruit pastes, nut caramel, effervescent powders, marzipan, persipan, (a marzipan substitute made from peach or apricot kernels), nougat, chocolates and coco products, lollipops, pastilles, chewing gum and the like. Products of the chewing gum type are particularly interesting, since such products are in contact with saliva for a long time and have a long residence time in the mouth. Although chewing gums are not usually swallowed, they are nevertheless regarded as foodstuffs in this context and thus fall within the concept of the invention.

Long-term contact in connection with relatively long residence times are understood as times of at least several minutes in the case of the products to be administered orally.

According to the invention, the foodstuff can also be an animal food.

According to another embodiment of an edible or oral composition of the invention, lactate dehydrogenase and the sucrose-inverting enzyme are added to pharmaceutical preparations as the active compound which can, of course, also be additionally present alongside other customary active compounds. Possible pharmacological preparations of this type, are, above all, tablets and dragees which contain sugars, in addition to the substances having a pharmaceutical action. Products which may be mentioned to which the invention is applicable are also various types of so-called quasi-medicinal products, such as, for example, cough mixtures or syrups and the like. Such products are frequently taken before going to bed, that is to say after the teeth have already been brushed, and thus have a long-term action on the film on the teeth. Mouth hygiene tablets in the broadest sense, such as dental hygiene dragrees and tablets for chewing, and tooth-cleansing chewing gums are preferred pharmaceutical preparaions within the scope of the invention. In this case also, the advantageous action of the active compound is based on the fact that because of insalivation in the oral cavity, an enzymatic protective film which is able to prevent the conversion of any residues of sugars present into cariogenic products can cover the teeth.

The dental hygiene agents mentioned can be, for example, in the form of a dental tablet which contains the customary polishing agents, binders, thickeners and humectants.

Examples of suitable polishing agents which can be used, for example, for dental hygiene agents are the customary calcium phosphates, such as tricalcium phosphate, alkali metal metaphosphates, magnesium carbonate, pulverulent plastics, such a polymethyl metacrylate (sic), urea/formaldehyde condensation products and the like, or mixtures of such substances.

In addition, the dental hygiene agents can also contain preservatives, aroma substances and other auxiliaries. In individual cases, however, it can also be desirable to assist or multiply the action of other active compounds, the aim of which is caries protection on the basis of other principles, by adding lactate dehydrogenase and a sucrose-inverting enzyme. Such customary active compounds which may be mentioned are, in particular, fluorine compounds, such as amine fluorides, alkali metal fluorides and the like, or dextranases.

The lactate dehydrogenase (also designated LDH in the following text) used according to the invention is commercially available. Lactate dehydrogenase can also be manufactured, inter alia, from various microbes, for example yeast. The LDH obtained from yeast is relatively stable, for example an enzyme preparation dissolved in glycerol remains active at $+18°$ C. for over one year. Moreover, LDH can also be stored for a relatively long time in buffer solutions within a defined pH range without an appreciable loss in activity. As experiments within the scope of the invention have shown, LDH incorporated in foodstuffs or pharmaceutical preparations of low water content or containing no water suffers only a relatively small loss in activity during customary storage times, if any loss occurs at all.

The sucrose-inverting enzyme used in the edible or oral compositions according to the invention is also commercially available. Possible sucrose-inverting enzymes within the scope of the invention are, above all, the saccharases, of which there may be mentioned the $\alpha$-glucosidases (sic) and, preferably, the $\beta$-fructosidases, which split sucrose into glucose and fructose. It is known that sucrose is split by $\alpha$-glucosidase, since it contains $\alpha$-glycosidically bonded glucose. However, sucrose can also be attacked by a second ferment, the action of which is determined by the fructose half of the molecule, which is contained in the form of $\beta$-fructofuranoside. This ferment is thus a $\beta$-fructosidase, which in many cases is also called $\alpha$-h-fructosidase (the h is intended to designate the furanose structure of the fructose). These enzymes are known, as a rule industrial preparations obtained from special yeast strains being commercially available. These enzymes have a good stability on storage; thus, for example, purified dried preparations of yeast invertase can be kept for at least 1 year. Furthermore, to a certain extent, storage in buffer solutions in a defined pH range for relatively long storage times can also give rise to no loss in activity [compare "Methoden der Enzymatischen Analyse" "(Methods of Enzymatic Analysis"), H. U. Bergmeyer, 3rd edition 1974, volume 1, Verlag Chemie, Weinheim, pages 951–963]. As experiments carried out within the scope of the invention have shown, sucrose-inverting enzyme incorporated in foodstuffs or pharmaceutical preparations of low water content or containing no water suffers only a very low loss in activity during customary storage times. Thus it was found, for example, that lyophilised $\beta$-h-fructosidase which had been incorporated, by stirring, into commercially available chocolate, rendered thermoplastic to some extent by increasing the temperature to 45° C., suffered, during this incorporation, a loss inactivity of only about 8%, which increased ton only about 15% on storage for 6 months.

It is preferable to choose the amount of enzyme activity incorporated, according to the storage time to be assumed for the material, so that, at the amount of eating, this is at least about adequate to cause the desired effect.

The amounts of lactate dehydrogenase and sucrose-inverting enzyme which are incorporated into the foodstuff, the confectionery or the pharmaceutical preparation, such as tooth-cleansing tablets, but in particular in hygiene agents in tablet form for dentures, can easily be determined by the expert on the basis of the specific enzyme activity, the approximate sugar content of the material, if there is one, and on the basis of the pH range in the binder or existing during its manufacture.

In general, an LDH amount of 0.2 mg–0.5 g/kg is suitable. 0.5 mg–0.05 g/kg (relative to the specific activity of about 300 U/mg) is preferably used.

In addition, the temperature and if appropriate the water content of the material on adding the enzyme and its customary storage temperature are also to be taken into consideration. The content of the two enzymes which is appropriately to be incorporated can also be determined by simple experimental batches. The amount of invertase is preferably in the range from 0.05 g–5.0 g/kg (relative to a specific activity of about 100 U/mg).

During determinations of the enzyme activity to be incorporated, it is not necessary, for example, to take into consideration all of the sucrose content, if appropriate even the latent sucrose content, which can be formed from precursors, such as starch and the like. According to experience, a relatively large amount of the food is swallowed, so that a large proportion of the sucrose no longer comes into contact with the teeth. It is sufficient, however, to take into consideration, with regard to the addition of amounts of enzyme, the portions of sucrose deposited on the teeth. If has been found, for example, by brushing the teeth and rinsing the mouth out with distilled water, that in an average of 50 experiments less than 1 g of sucrose could be detected in the rinsing liquid when the experimental subjects had first been given about 50 g of commercially available chocolate. Lastly, however, only this proportion of residual sugar remaining or to be expected in the oral cavity is to be focused on, so that if the same proportion of enzymes is not also swallowed with the chewed food, they can be employed in an activity amount which is less than proportional compared with the starting amount of sugars. It also applies to pharmaceutical preparations, and in particular dental hygiene agents or mouth hygiene agents, into which lactate dehydrogenase and a sucrose-inverting enzyme can be incorporated, that the amounts of enzymes to be incorporated are determined by rough calculations or empirical experiments. In dental hygiene agents and mouth hygiene agents of this type, there is usually no sugar content, for which reason it is not necessary to orientate the enzyme activities to be incorporated with respect to this sugar content. In this case, incorporation of the abovementioned enzymes has the purpose of producing a caries-inhibiting liquid film in the oral cavity, especially on the teeth, so that any food residues remaining, which are not removed even by brushing, cannot lead to caries in the presence of cariogenic bacteria.

The ratio of the amount of the enzyme lactate dehydrogenase incorporated to the amount of sucrose-inverting enzyme can vary within a wide range. The amount of sucrose-inverting enzyme should be sufficient to effect inversion of the sucrose content. The amounts determined by calculation or by simple experimental batches are as a rule condierable higher than those proportions which have proved advantageous for the simultaneous use of LDH.

Intensification of the lactate dehydrogenase action by adding a suitable hydrogen acceptor, for example nicotin-amide-adenine dinucleotide, can also be envisaged according to the invention.

The incorporation of the enzyme lactate dehydrogenase together with the sucrose-inverting enzyme is appropriately carried out in a manner such that a homogeneous distribution of the enzymes within the foodstuff results. On the other hand, it can also be preferably, especially if the foodstuff itself contains no isotropic distribution of sugar, likewise to provide a nonuniform distribution of the enzymes incorporated. Thus, for example, in the case of chocolate mixed with whole nuts, it would not be necessary to also homogeneously mix the nut constituent of the chocolate with enzymes.

The incorporation of lactate dehydrogenase and the sucrose-inverting enzymes is usually carried out at a pH value at which these ensymes are stable, and at a temperature at which the activity of the enzymes is not impaired. A preferred pH range is between pH 4 and 7, and a range from 4.7–5.2 is particularly advantageous. It is particularly preferably to incorporate the two enzymes into the foodstuff and the like at the pH range which is between the stability optima of the enzymes. Suitable incorporation temperatures are between 0° and 50° C., and temperatures between 20° and 50° C. are to be regarded as particularly favourable. The temperature range from 20° to 40° C. is particularly preferred, depending on the intended use.

It can be desirable, depending on the nature of the medium, to add the enzymes either in the course of the manufacturing process or after finishing the foodstuff or the pharmaceutical preparations, if, for example, no significant amount of water is still present. In the case of confectionery such as chocolate bars, chocolates and the like, it is preferably to add the enzyme only at a relatively late point in time so that no losses in activity during the course of the production of the confectionery result.

In the following text, experiments are described which demonstrate the anti-catiogenic action when lactate dehydrogenase is added in combination with a sucrose inverting enzyme:

A commercially available, fat-containing and sugar-containing spread of low water content was used as the cariogenic substrate. White, homozygous rates of the "Wistar" type were used as the experimental animals. The spread mentioned was admixed in an amount of 50% of the total amount to a standard dry feed (Herilan-RM 20), consisting of a vitamin-rich protein/fat diet which has been developed taking into consideration all the metabolism requirements of rates.

The air dried experimental diet was proportioned and metered so that the animals could further increase in weight during the feeding period of 280 days. The animals were kept in plastic cages which were each provided with drinking and feeding machines. 50 to $60 \times 10^3$ Streptococci (sic) mutans germs per milliliter were added to the drinking water in each case at intervals of 30 days. Sterilised fine wood granules which were replaced at intervals of 36 hours were used as the litter. The room was air-conditioned.

The animals were divided into experimental groups consisting of 60 animals each. All the animals were inspected daily and weighed at intervals of 30 days, during which no side-effects at all from the content of LDH and sucrose-inverting enzyme could be detected.

The appearance of caries, in particular of carious lesions, was established by means of a stereomicroscope with a magnification of 12:

The following gradings were recorded:
0 = no caries
1 = 1 to 5 lesions
2 = 5 to 10 lesions
3 = more than 10 lesions The following diet compositions were tested:
A = 50% of dry feed + 50% of spread
B = 50% of dry feed + 50% of spread + lactate dehydrogenase and sucrose-inverting enzyme (commercially available β-h-fructosidase)

The amount of lactate dehydrogenase was 0.5 mg per kg of spread and the amount of sucrose-inverting enzyme was 0.3 g per kg of spread.

When diet A was administered, numerous carious lesions occurred: 30 (50%) of the animals were affected. The experimental results with regard to the number of lesions and also the degree of severity in each case are summarised in the table which follows. As the results shown, lesions which in some cases were very severy (>10) were found in the experimental animals fed with diet A. In the case of diet B, both the number and the degree of severity of the lesions were drastically reduced by adding LDH in combination with the sucrose-inverting enzyme. The results clearly show the non-cariogenic action which is not harmful to teeth, of the diet provided with lactate dehydrogenase and the sucrose-inverting enzyme.

TABLE

| Experimental group | Caries lesions (number × degree) |
|---|---|
| A (diet A) | 15 × 1; 9 × 2; 6 × 3 |
| B (diet B) | 4 × 1 |

Further exampled of foodstuffs and pharmaceutical preparations which contain LDH and a sucrose-inverting enzyme are given in the following text.

1. Milk chocolate bar

| containing | | |
|---|---|---|
| | cocoa substance | 26 g |
| | sucrose | 60 g |
| | milk fat | 3.2 g |
| | fat-free dry substance and | 9.5 g |
| | lactate dehydrogenase and | about 5–10 mg |
| | β-h-fructosidase, | about 20–25 mg |
| | which were stirred in, to form a homogenous distribution, at about 40–45° C. before cooling the finished chocolate. | |

2. Sweetening tablets

| containing | | |
|---|---|---|
| | xylitol | 5 g |
| | the sodium salt of saccharin | 0.7 g |
| | sodium cyclamate | 0.3 g |
| | lactate dehydrogenase (commercial product) | 0.1–0.5 mg |
| | invertase (freese-dried commercial product) | 30 mg |

For use, the above dry mixture can also be converted into the form of a low-calorie, anti-cariogenic sweetening solution by adding water.

3. Tooth-cleansing dragee

| | | % by weight |
|---|---|---|
| containing | magnesium carbonate | 10.0 |
| | silicon dioxide | 20.0 |
| | dicalcium phosphate | 55.0 |
| | a urea/formaldehyde condensate | 5.50 |
| | aroma substances | 2.0 |
| | tragacanth | 1.5 |
| | sodium lauryl-sulphoacetate | 2.5 |
| | a long-chain amine fluoride | 2.0 |
| | lactate dehydrogenase | 0.1 |
| | β-h-fructosidase | 0.3 |

4. Anti-cariogenic chewing gum 0.002 part of antimicrobially active sodium hexametaphosphate, 10 mg of commercially available LDH and 50 mg of invertase (freeze-dried commercial product, manufacturer: Serva, Heidelberg) were additionally incorporated into a customary chewing gum base (1 kg; 25 parts of coumarone resin, 40 parts of gum, 10 parts of paraffin wax, 15 parts of dry latex, 67 parts of sorbitol powder, 0.1 part of sodium cyclamate and 1 part of aroma substances). The mass was thoroughly mixed and, after rolling out into strips, cut.

What we claim is:

1. An edible or oral low moisture content composition which composition contains sugar, sugar substitutes or no sugar and a content of the enzymes lactate dehydrogenase and sucrose-inverting enzyme sufficient to limit promotion of tooth decay.

2. A compositon according to claim 1 which contains sucrose.

3. A composition according to either of claims 1 or 2 in which the content of the enzymes lactate dehydrogenase and sucrose-inverting enzyme is at least sufficient to prevent the formation of cariogenic decomposition products or of products promoting caries.

4. A composition according to claims 1 or 2 which further contains a suitable hydrogen acceptor to intensify the effects of the content of lactate dehydrogenase.

5. A composition according to any one of claims 1 or 2 wherein the enzyme is β-fructosidase or α-glucosidase.

6. A composition according to any one of claims 1 or 2 which is a food.

7. A composition according to any one of claims 1 or 2 which is a pharmaceutical composition for tooth or mouth care.

8. A method for the production of an edible or oral low moisture content composition which contains sugar, sugar substitutes or no sugar and which comprises adding lactate dehydrogenase and sucrose-inverting enzyme to the composition during or after the production of the composition in an amount sufficient to limit promotion of tooth decay.

9. A method according to claim 8 wherein the enzymes are introduced into the composition to achieve a homogeneous distribution.

10. A method according to either of claims 8 or 9 wherein the composition is kept at pH-values for enzyme stability or under conditions of optimal enzyme stability during the time the enzymes are added.

11. A method according to claim 10 wherein the composition is kept at a pH of from 4 and 7 during the time the enzymes are added.

12. A method according to claim 12 wherein the pH is from 4.7 to 5.2.

13. A method according to any one of claims 8 or 9 wherein the composition is kept at a temperature of from 20 to 50 degrees Centigrade during the time the enzymes are added.

14. A method according to any one of claims 8 or 9 wherein the sucrose-inverting enzyme is β-fructosidase or α-glucosidase.

15. A method according to claim 10 wherein a suitable hydrogen acceptor is added to intensify the effects of the lactate dehydrogenase.

16. An edible or oral composition when produced by a method according to any one of claims 8 or 12.

17. A composition according to claim 3 which further contains a suitable hydrogen acceptor to intensify the effects of the content of lactate dehydrogenase.

18. A composition according to claim 3 wherein the enzyme is β-fructosidase or α-glucosidase.

19. A composition according to claim 4 wherein the enzyme is β-fructosidase or α-glucosidase.

20. A composition according to claim 3 which is a food.

21. A composition according to claim 4 which is a food.

22. A composition according to claim 5 which is a food.

23. A composition according to claim 3 which is a pharmaceutical composition for tooth or mouth care.

24. A composition according to claim 4 which is a pharmaceutical composition for tooth or mouth care.

25. A composition according to claim 5 which is a pharmaceutical composition for tooth or mouth care.

26. A method according to claim 10 wherein the composition is kept at a temperature of from 20°–50° C. during the time the enzymes are added.

27. A method according to claim 11 wherein the composition is kept at a temperature of from 20°–50° C. during the time the enzymes are added.

28. A method according to claim 12 wherein the composition is kept at a temperature of from 20°–50° C. during the time the enzymes are added.

29. A method according to claim 10 wherein the sucrose-inverting enzyme is β-fructosidase or α-glucosidase.

30. A method according to claim 11 wherein the sucrose-inverting enzyme is β-fructosidase or α-glucosidase.

31. A method according to claim 12 wherein the sucrose-inverting enzyme is β-fructosidase or α-glucosidase.

32. A method according to claim 13 wherein the sucrose-inverting enzyme is β-fructosidase or α-glucosidase.

33. A method according to claim 10 wherein a suitable hydrogen acceptor is added to intensify the effects of the lactate dehydrogenase.

34. A method according to claim 11 wherein a suitable hydrogen acceptor is added to intensify the effects of the lactate dehydrogenase.

35. An edible or oral composition produced by a method according to claim 10.

36. An edible or oral composition produced by a method according to claim 11.

37. An edible or oral composition produced by a method according to claim 13.

38. An edible or oral composition produced by a method according to claim 14.

39. An edible or oral composition produced by a method according to claim 15.

40. An edible or oral composition produced by a method according to claim 8.

41. An edible or oral low moisture content composition which contains sugar, sugar substitute or no sugar and a content of the enzymes lactate dehydrogenase and sucrose-inverting enzyme which limits the promotion of tooth decay and wherein the lactate dehydrogenase is present in a range of from about 0.2 mg to about 0.5 g per kg relative to a specific activity of about 300 U/mg of composition and wherein the sucrose-inverting enzyme is present in an amount from about 0.05 g to 5.0 g per kg of composition relative to a specific activity of about 100 U/mg.

42. A composition according to claim 41 wherein the lactate dehydrogenase is present in an amount from about 0.5 mg–0.05 g per kg of composition relative to a specific activity of about 300 U/mg.

43. A composition according to claim 1 which further contains nicotin-amide-adenine dinucleotide as a hydrogen acceptor.

44. An edible low moisture content composition which composition contains sugar and a content of the enzyme lactate dehydrogenase and sucrose-inverting enzyme sufficient to limit the promotion of tooth decay.

45. A composition according to claim 1 which is a tooth-cleansing dragee comprising magnesium carbonate, silicon, dioxide, dicalcium phosphate, a urea-formaldehyde condensate, a long-chain amine fluoride, lactate dehydrogenase, and β-h-fructosidase.

* * * * *

UNITED STATES PATENT OFFICE
CERTIFICATE OF CORRECTION

Patent No. 4,255,414     Dated March 10, 1981

Inventor(s) Lembke, Andreas; and Gorny, Dietrich

It is certified that error appears in the above-identified patent and that said Letters Patent are hereby corrected as shown below:

IN THE SPECIFICATION:

Column 5, line 4, "pharmacological" should be --pharmaceutical--.

Column 5, line 7, "pharmaceutical" should be --pharmacological--.

IN THE CLAIMS:

Claim 12. - "claim 12" should be --claim 11--

Claim 16. - "any one of claims 8 or 12" should read --any one of claims 8, 9 or 12--

Signed and Sealed this

Fifth Day of January 1982

[SEAL]

Attest:

GERALD J. MOSSINGHOFF

Attesting Officer     Commissioner of Patents and Trademarks